United States Patent [19]
Margolin

[11] Patent Number: 5,248,303
[45] Date of Patent: Sep. 28, 1993

[54] MEDICAL SYRINGE WITH NEEDLE-RETRACTING MECHANISM

[76] Inventor: George D. Margolin, 308 Vista Baya, Costa Mesa, Calif. 92627

[21] Appl. No.: 909,787

[22] Filed: Jul. 7, 1992

Related U.S. Application Data

[63] Continuation-in-part of Ser. No. 750,209, Aug. 27, 1991, abandoned.

[51] Int. Cl.⁵ ............................................. A61M 5/00
[52] U.S. Cl. ................................ 604/187; 604/197; 604/204; 604/212; 128/919
[58] Field of Search ........ 604/110, 111, 187, 192–198, 604/200, 201, 204, 205, 206, 212, 232–234, 239, 272; 128/919; 222/105, 183

[56] References Cited

U.S. PATENT DOCUMENTS

| | | | |
|---|---|---|---|
| 3,276,632 | 10/1966 | Stanzel | 604/204 X |
| 3,736,933 | 6/1973 | Szabo | 604/212 X |
| 4,573,977 | 3/1986 | Crawford | 604/212 |
| 5,007,903 | 4/1991 | Ellard | 604/195 |
| 5,019,048 | 5/1991 | Margolin | 604/153 |

FOREIGN PATENT DOCUMENTS

| | | | |
|---|---|---|---|
| 1537267 | 1/1990 | U.S.S.R. | 604/196 |
| 0789029 | 1/1958 | United Kingdom | 604/200 |
| 1232407 | 5/1971 | United Kingdom | 604/200 |

*Primary Examiner*—C. Fred Rosenbaum
*Assistant Examiner*—Mark O. Polutta
*Attorney, Agent, or Firm*—Herbert M. Shapiro

[57] ABSTRACT

A unit dose syringe comprises a fluid-containing plastic bag with an attached needle and a dimensionally-stable shell like a woman's compact. The shell contains a thumb-operated slider assembly for advancing the needle to an exposed position for fluid delivery. The syringe also includes a spring-biasing arrangement to return the needle, automatically, to the protected position, after use, and a means for rupturing the bag and retaining the needle in the protected position.

7 Claims, 4 Drawing Sheets

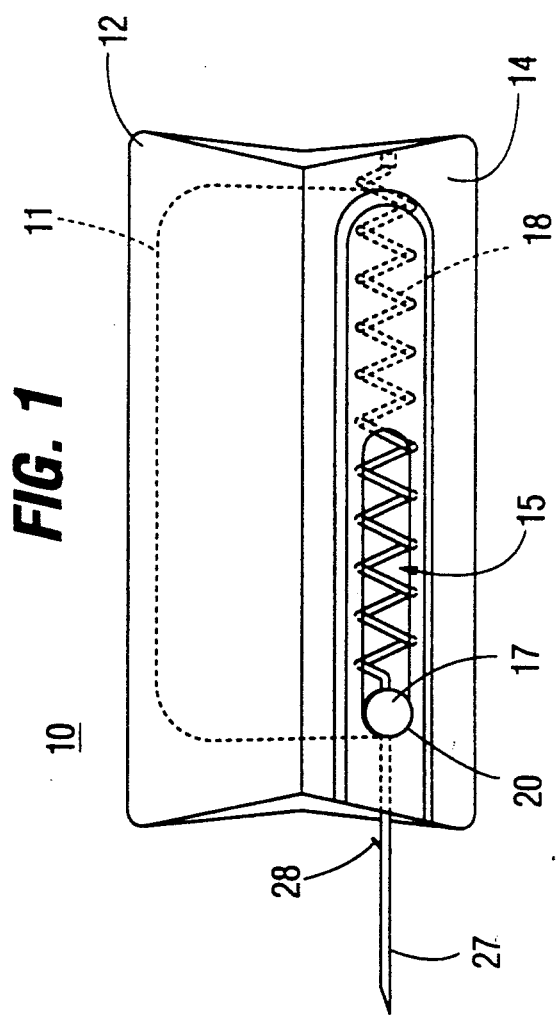
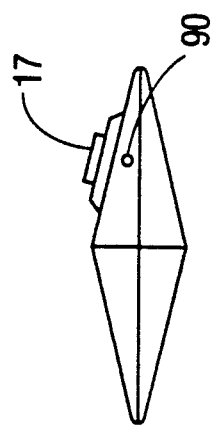
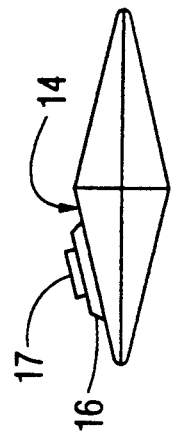
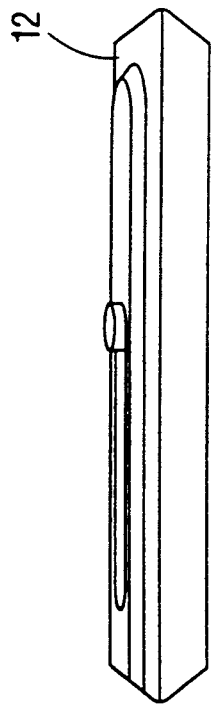

MEDICAL SYRINGE WITH NEEDLE-RETRACTING MECHANISM

RELATION TO OTHER PATENT APPLICATION

The present patent application is a continuation in part of patent application Ser. No. 07/750,209 filed Aug. 27, 1991 abandoned for the applicant in the present application.

FIELD OF THE INVENTION

This invention relates to syringes for use in delivering medicine to a user, and more particularly to such syringes incapable of being reused.

RELATION TO OTHER PATENT APPLICATION

BACKGROUND OF THE INVENTION

U.S. Pat. No. 4,019,048, issued May 28, 1991, to the inventor of the present invention, discloses a unit dose syringe which employs a baggie for forming a compartment for containing fluid (medicine) and a needle movable to an exposed position for administering the fluid. The needle, once used, is returned to a protected position, an action which ruptures the baggie and prevents reuse.

BRIEF DESCRIPTION OF AN EMBODIMENT OF THIS INVENTION

A fluid pouch or baggie and needle are enclosed in a shell like a women's miniature compact. The needle is spring biased into a position totally within the compact. A thumb-operated slider is exposed at the surface of the shell. The slider is advanced to extend the needle into an exposed position for delivering the fluid. Release of the slider permits the spring-loaded needle, or spring-loaded slider mechanism, to retract the needle into a protected position. A detent captures the retracted needle or slider to prevent reuse and the operation of returning the needle to the protected position ruptures the baggie again to prevent reuse.

The spring-loaded needle and slider mechanism for single use operation is considered a significant departure from prior art thinking along with operator-controlled operation.

BRIEF DESCRIPTION OF THE DRAWING

FIGS. 1, 2, 3, and 4 are schematic plan, side, back, and front views of a syringe in accordance with the principles of this invention;

DETAILED DESCRIPTION OF AN ILLUSTRATIVE EMBODIMENT OF THIS INVENTION

Figure 6:
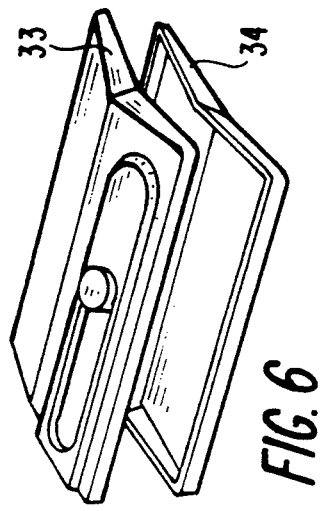
FIGS. 5, 6, and 7 are schematic views of a portion of the syringe of FIG. 1 showing the syringe during assembly.

FIG. 1 shows a syringe 10 in accordance with the principles of this invention. The syringe includes a fluid sac or baggie 11 and a shell 12. Face portion 14 of shell 12 has an opening 15 defined in it. Slider assembly 16 is secured within opening 15. The slider assembly includes a button 17 secured to a needle. The button is biased into the position shown for it in FIG. 1 against spring 18.

FIGS. 2, 3, and 4 show side, back, and front views of the shell. The slider assembly can be seen to extend outwards of the face (14). When button 17 is moved, by thumb, to the left to position 20, the needle 27 advances to an exposed position as indicated in FIGS. 1 and 4.

After the syringe is used to administer fluid contents of the baggie, accomplished by compressing shell 12 and thus baggie 11, the thumb disengages button 17 and spring 18 retracts the needle to the protected position. Needle 27 includes a rearward-extending barb 28 operative to rupture the baggie as the needle retracts. Also, button 17, when advanced, engages a detent (not shown) which prevents spring 18 from retracting the slider further to the right than the position shown for the button in FIG. 1. The movement of the button to the left engages the detent so that the button (or needle or both) is retracted, after use, to a lock position further to the right of the initial position.

Figure 7:
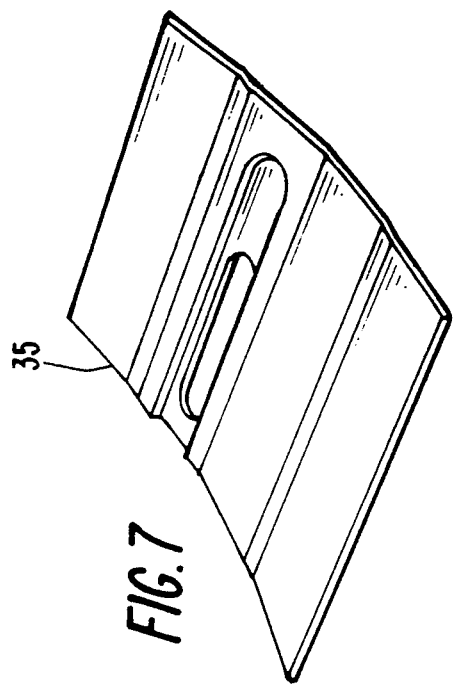
Figure 5:
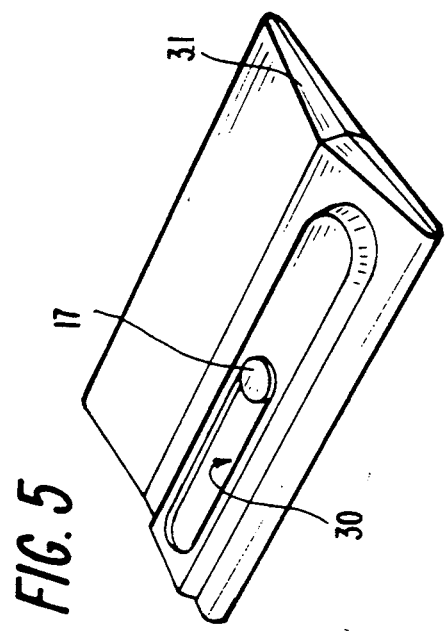

The shell of FIG. 1 is shown in FIG. 5. The button (17) moves to the left through space 30, the underside of which is protected by a foil. The shell can be seen to have a shallow v-shaped roof top portion 31 and can be made in two pieces as shown in FIG. 6 as portions 33 and 34. Alternatively, the shell can be made as a single folded piece 35 as shown in FIG. 7.

The entire syringe is small, having dimensions of about two inches by slightly over one inch (1.13 inch) by 0.125 inch. The sac conveniently is a plastic baggie and the shell is made of cardboard- similar to an ice cream cum material. A syringe of such dimensions defined a 3 cc volume.

Such a syringe can be seen to be very inexpensive to manufacture, safe to dispose of, and operable only a single time.

Figure 8:
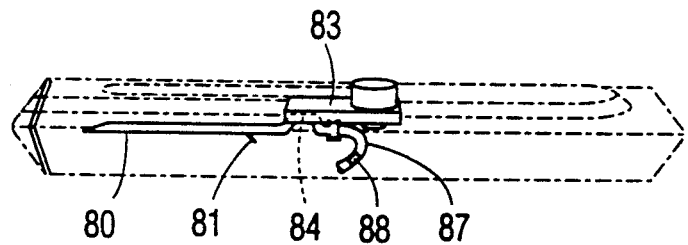
FIGS. 8-13 are schematic representations of various elements of the syringe of FIGS. 1, 2, and 3.

FIGS. 8 through 13 show the details of various elements of one embodiment of the syringe. Specifically, FIG. 8 shows a needle 80 with a rearward extending barb 81. The needle is attached to slider 83 along area 84 by cement, clamping, etc. The rear end of the needle is enlarged as shown at 85 in FIG. 9 and is shrink fitted to sac 87 as shown in FIG. 8. Sac 87 conveniently includes an overpressure valve 88, shown in FIGS. 8 and 10, operative normally to retain fluids in the sac and to permit passage of the fluids when the shell is squeezed.

Figure 9:
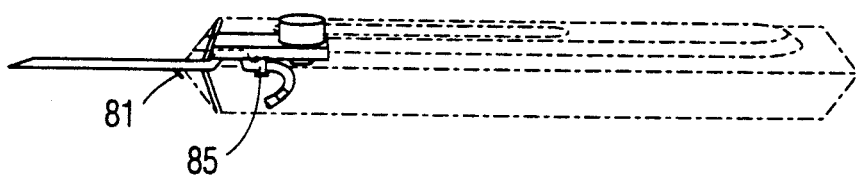

In operation, when the slider is advanced from the position shown in FIG. 8 to the position shown in FIG. 9, the point of the needle passes through hole 90 of FIG. 4. Hole 90 is covered with an adhesive seal 91 of FIG. 11 which is removed prior to use to ensure cleanliness.

Figure 12:
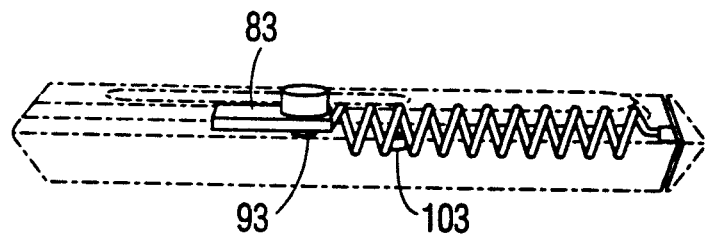

Slider 83 includes a support 93 as shown in FIG. 12. Spring 18 of FIG. 1 is connected to this support as shown in the figure. The opposite end of spring 18 is connected to a similar support which is part of the rear wall of the shell as shown in FIG. 12. When the slider is advanced to the position shown in FIG. 9, spring 18 is stretched as shown in FIG. 12 and retracts the slider when released.

Figure 13:
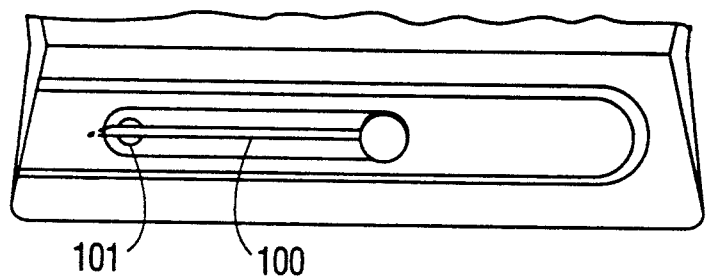

In a preferred embodiment, the guide 100 of FIG. 13 includes a recess 101 which captures button 17 of FIG. 5 when the slider is advanced to the position shown in FIG. 9. The spring support 93 of FIG. 12 is made of a geometry to elevate the button out of the recess 101 when the shell is squeezed after delivery of the contents of the sac. Thus, the needle is in a fixed position for insertion, yet released during operation for withdrawal of the needle back into the shell whenever the operator's thumb is withdrawn from button 17.

Figure 10:
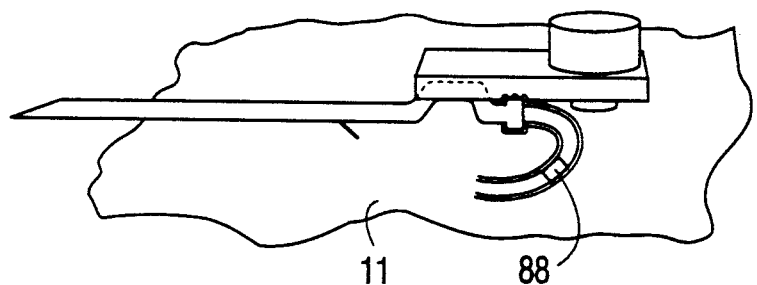
Figure 11:
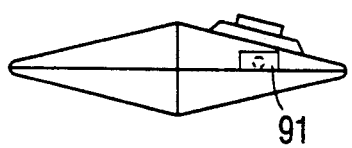
Figure 14:
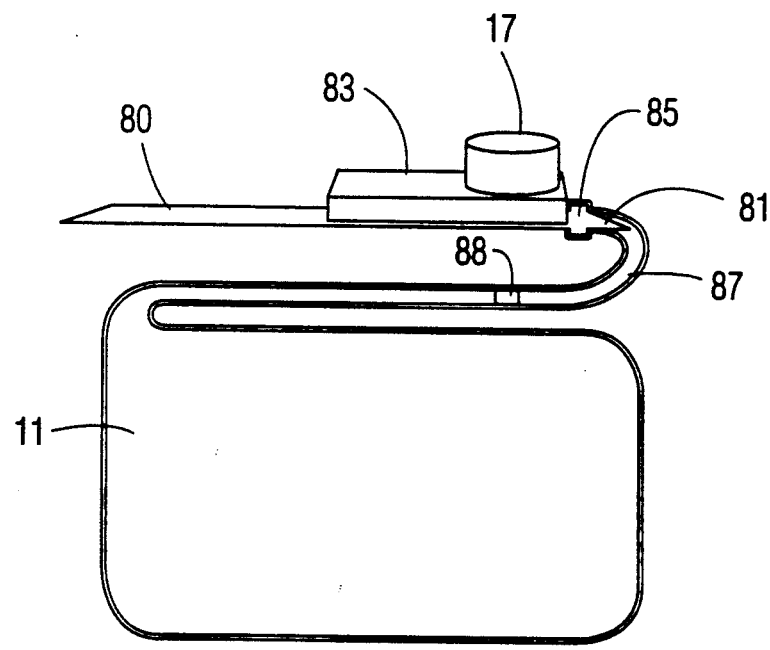
FIG. 14 is a schematic representation of an embodiment of this invention in which the elements of FIGS. 8, 9, and 10 are organized in a practical application.

FIG. 14 shows the various elements of FIGS. 8, 9, and 10 organized in a practical embodiment. In this embodiment, the barb 81 extends from the rear of the needle 80.

When the slider is withdrawn back into the shell, support 93 drops into aperture 103 which operates as a detent to constrain the slider from being extended again.

In an alternative embodiment, such a detent is not necessary. Instead, the sac may be loose in the shell. Once the needle has been retracted, the sac cannot be refilled because it no is longer in a condition to be filled by the expanding action of the shell to which it is not attached. The only time the sac need be returned or the needle restrained from being extended is in embodiment where the sac is attached to the shell permitting the practice of a sucking feature. This would permit the syringe to be filled or refilled in a normal fashion by increasing the volume of the sac since it would be attached to the shell and would follow the movement of the shell.

What is claimed is:

1. A unit dose syringe comprising a compressible fluid-containing sac and a needle communicating with said sac, said syringe also including a dimensionally-stable shell for enclosing said sac and needle, said shell including hand-operated means engaging said needle for moving said needle from a protected position within said shell to an extended position beyond said shell for delivery of said fluid, said shell being compressable for delivering fluid through the extended needle, said means for moving including operator-initiated means for returning said needle to said protected position.

2. A syringe as set forth in claim 1 wherein said operator-initiated means includes a spring for biasing said needle into said protected position.

3. A syringe as set forth in claim 2 also including means responsive to the movement of said needle from said exposed to said protected position for rupturing said sac.

4. A syringe as set forth in claim 2 also including means responsive to the movement of said needle from said exposed to said protected position for preventing further movement of said needle to said exposed position.

5. A syringe as set forth in claim 3 also including means responsive to the movement of said needle from said exposed to said protected position for preventing the further movement of said needle to said exposed position.

6. A syringe as set forth in claim 5 wherein said means for engaging said needle is a slider for moving said needle along an axis between said protected and said exposed position.

7. A syringe as set forth in claim 6 wherein said means responsive to the movement of said needle comprises a detent in said slider's path, said detent in said protected position engaging said slider to prevent further needle movement.

* * * * *